United States Patent
Honkura (10) Patent No.: US 10,398,341 B2
(45) Date of Patent: Sep. 3, 2019

(54) MAGNETIC GRADIOMETER ELEMENT AND MAGNETIC GRADIOMETER

(71) Applicant: MAGNEDESIGN CORPORATION, Aichi-Ken (JP)

(72) Inventor: Yoshinobu Honkura, Aichi-Ken (JP)

(73) Assignee: MAGNEDESIGN CORPORATION, Aichi-Ken (JP)

( * ) Notice: Subject to any disclaimer, the term of this patent is extended or adjusted under 35 U.S.C. 154(b) by 221 days.

(21) Appl. No.: 15/288,529

(22) Filed: Oct. 7, 2016

(65) Prior Publication Data

US 2017/0100051 A1    Apr. 13, 2017

(30) Foreign Application Priority Data

Oct. 11, 2015 (JP) ................................. 2015-201633
Apr. 30, 2016 (JP) .................................. 2016-92198

(51) Int. Cl.
*A61B 5/05* (2006.01)
*G01R 33/022* (2006.01)
*A61B 5/04* (2006.01)

(52) U.S. Cl.
CPC ............ *A61B 5/05* (2013.01); *A61B 5/04005* (2013.01); *G01R 33/022* (2013.01); *A61B 5/04007* (2013.01); *A61B 5/04008* (2013.01); *A61B 2562/0223* (2013.01)

(58) Field of Classification Search
CPC .. A61B 5/05; A61B 2562/0223; G01R 33/022
USPC ........................ 600/409, 407; 324/252, 249
See application file for complete search history.

(56) References Cited

U.S. PATENT DOCUMENTS

| 6,121,770 | A  | * | 9/2000  | Sudo    | G01R 33/02   |
|           |    |   |         |         | 324/244      |
| 6,424,853 | B1 | * | 7/2002  | Tsukada | A61B 5/04005 |
|           |    |   |         |         | 324/248      |
| 7,181,857 | B2 | * | 2/2007  | Lee     | G01C 17/30   |
|           |    |   |         |         | 33/356       |
| 8,587,300 | B2 | * | 11/2013 | Honkura | G01R 33/063  |
|           |    |   |         |         | 324/252      |
| 2001/0030537 | A1 | * | 10/2001 | Honkura | G01R 33/02 |
|           |    |   |         |         | 324/249      |
| 2003/0052671 | A1 | * | 3/2003 | Kawase  | G01C 17/30   |
|           |    |   |         |         | 324/249      |

(Continued)

FOREIGN PATENT DOCUMENTS

JP    2012-245373 A    12/2012
JP    2015-059823 A    3/2015

OTHER PUBLICATIONS

Uchiyama, Miyazaki, "The development of ultra-high sensitive gradiometer to detect living body magnetism" presented in JST meeting in 2011, 9 pages.

*Primary Examiner* — Christopher W Fulton
(74) *Attorney, Agent, or Firm* — Nelson Mullins Riley & Scarborough LLP; Anthony A. Laurentano (57) ABSTRACT

The gradiometers of the present invention are developed by applying GSR sensors to have the detectability of magnetic field same to that of SQUID without a cryogenic temperature retainer. Plural GSR elements are fitted on two parallel convex line guides of the gradiometer board using two parallel concave line guides of the GSR element board to keep the parallel among wires direction of GSR elements perfectly and to cancel the outside magnetic field noise without a magnetic shield room.

9 Claims, 7 Drawing Sheets

(56) References Cited

U.S. PATENT DOCUMENTS

| | | | |
|---|---|---|---|
| 2003/0155913 A1* | 8/2003 | Honkura | G01R 33/02 324/249 |
| 2005/0072011 A1* | 4/2005 | Miyashita | G01C 17/30 33/355 R |
| 2007/0222441 A1* | 9/2007 | Satoh | G01R 33/0206 324/253 |
| 2010/0026288 A1* | 2/2010 | Sauber | B82Y 25/00 324/252 |
| 2011/0285395 A1* | 11/2011 | van Veldhoven | G01R 33/09 324/252 |
| 2012/0151786 A1* | 6/2012 | Ohmori | G01C 17/30 33/361 |
| 2015/0008913 A1* | 1/2015 | Fu | G01R 33/096 324/252 |
| 2015/0108974 A1* | 4/2015 | Kennedy | G01R 33/09 324/252 |
| 2016/0169838 A1* | 6/2016 | Nagarkar | G01R 33/096 600/301 |
| 2016/0187433 A1* | 6/2016 | Nishimura | G01R 33/063 324/252 |
| 2016/0238673 A1* | 8/2016 | Honkura | G01R 33/06 |
| 2017/0160351 A1* | 6/2017 | Yamamoto | G01C 17/30 |

* cited by examiner

MAGNETIC GRADIOMETER ELEMENT AND MAGNETIC GRADIOMETER

BACKGROUND OF THE INVENTION

Technical Field

This invention relates to magnetic gradiometer elements and magnetic gradiometers to detect living body magnetism of an ultra-minute magnetic field with a sharp magnetic gradient.

Background Art

SQUID equipment for detecting living body magnetism is widely used as diagnosis equipment such as magneto cardiogram and magnetoencephalography. Though SQUID has an ultra-high sensitivity in magnetic field detection, it needs a cryogenic temperature retainer and a magnetic shield room. It means that it is too expensive to spread this diagnostic technology. If a handy-type equipment to detect living body magnetism is developed, it will make popular diagnosis equipment.

However, the SQUID equipment has some problems besides being expensive. The first problem is that a magnetic field detection part of SQUID cannot be placed close to a surface of a living body and it can be placed at most at the distance of about 50 mm from the body, because it is contained in a cryogenic temperature retainer. The second problem is that its diameter is too big to make a fine pitch array arrangement and it cannot display fine images with very small pixels for magneto cardiogram or magnetoencephalography. The third problem is that it is difficult to detect living body magnetism three-dimensionally by arranging a magnetic field detection part along perpendicular direction of Z-axis against the horizontal direction formed by X-axis and Y-axis. The last one is that it is difficult to specify the depth position of the signal source because plural magnetic field parts cannot be arranged in the direction of Z-axis.

To solve the above weak points of SQUID equipment for detecting living body magnetism, a lot of efforts have been made to develop an ultra-sensitive micro magnetic sensor that detects living body magnetism using FG sensor, MI sensor, GSR sensor based on GHz-Spin-Rotation effect, and tMR sensor. FG sensor and MI sensor can detect living body magnetism of 5 pT-level using mechanical coil, but its size and price as well as the detectability is not sufficient. MI sensor and tMR sensor using micro elements produced by photolithography method have advantage in size and cost, but the detectability to detect living body magnetic fields is poor beyond 100 pT level at this moment.

A differential type of element or a gradiometer-type element is considered to be effective in theory to omit the magnetic shield room but still presents difficult technical problems. Nowadays many research projects have been carried out with trial and error. Patent Document 1 shows a biomedical signal detecting equipment in which a magnetic head has a magnetism detecting part with 1-cm amorphous wire and a pulse generator or high frequency generator. The detecting level of biomagnetism signal is 100 pT.

Patent Document 2 shows a magnetic coupling type gradiometer to measure the gradient of magnetic field strength. The distance between its detecting part and the object to be detected along the amorphous wire is about 150 mm and living body magnetism is not its target.

Non-Patent Document 1 shows a differential-type MI element in which two MI elements are arranged by mechanical ways along a reference line to detect the difference in magnetic field strength between both elements. It achieves a detectability of 10 pT-level which is not sufficient for measuring living body magnetism. Because the mechanical assembly cannot make arrangement with no displacement mismatch between both elements and remains several microns slide against a base line.

There is a need to develop handy-type body equipment to detect living body magnetism which has detectability of magnetic field equivalent to that of the SQUID type equipment and is free from cryogenic temperature retainer and magnetic shield room as well as advantages which are high array density, 3-axis magnetic field detection and the depth position detection of the signal source. It is also a key to invent a magnetic gradiometer element of use in that.

CITATION LIST

Patent Documents

Patent Document 1: Japanese Unexamined Patent Application Publication No. 2012-245373
Patent Document 2: Japanese Unexamined Patent Application Publication No. 2015-059823

Non-Patent Documents

Non-Patent Document 1: "The development of ultra-high sensitive gradiometer to detect living body magnetism" presented by Uchiyama, Miyazaki in JST meeting in 2011.

SUMMARY OF INVENTION

Technical Problems

The study for the present invention was carried out to develop a three dimensional-type gradiometer with high density array arrangement using GSR sensor element (hereafter "GSR element") with detectability of less than 1 pT level in the magnetic shield room. As used herein, "GSR" means GHz-Spin-Rotation effect.

The main problems of this study are as follows:
(1) Detecting less than 1 pT level living body magnetism without magnetic shield;
(2) Computing the depth position by arranging more than three elements along Z-axis direction;
(3) Measuring the magnetic gradient not only of the direction of Z axis but also of the direction of X axis and Y axis toward Z-axis direction; and
(4) Obtaining the fine magnetic image mapping on the cross section of the living body with high-density pixels.

The main problems are discussed in detail below.

The first problem is how to measure body magnetism of less than 1 pT level using GSR sensor without a magnetic shield room for omitting the noise of the outer magnetic field. If plural GSR elements can be arranged with no displacement or no slide against a reference line along the direction of Z axis on the base plane, the outer magnetic noise must be cancelled perfectly with the same level to the magnetic shield room. The conventional mechanical assembling methods along the marked reference line on the base plane meet the precision limitation on slide displacement of ±5 μm and angle mismatch of ±0.1 degree which produce insufficient canceling the outer magnetic noise. The new assembling method to obtain slide displacement of ±1 μm and angle mismatch of ±0.01 degree is required for omitting the noise of the outer magnetic field perfectly.

The second problem is how to detect the depth of a magnetic source in a living body. More than three GSR elements arranged along the Z-axis direction can measure the living body magnetism with the magnetic field gradient, which depends on the distance. Using the data, the depth position can be computed from the functional relationship between the measured value of the magnetic field and the distance.

The source of a cardiac magnetic field or brain magnetic field is placed from 10 mm to 40 mm below the body surface. More than three GSR elements consisting of magnetic gradiometer element to detect the source should be set from less than 5 mm up to 40 mm in the distance from the body surface.

Because GSR element is less than 3 mm in length, it is possible to produce the gradiometer element having more than three GSR elements set at a place from less than 5 mm to 40 mm on a straight line along Z axis. A difficult point is how to set more than three GSR elements at the position from living body with the accuracy of less than ±1 µm. By the way, the other sensor elements such as FG sensor and MI sensor have too long lengths of about 20 mm to 40 mm to arrange more than three elements within the length of magnetic gradiometer element of up to 40 mm.

The third problem is how to measure the magnetic gradient toward the direction of Z axis of not only Z axis direction magnetic field but also X axis and Y axis directions of magnetic field. If 3 dimensional gradiometer element with new arrangements of more than three elements for measuring X axis and Z axis magnetic field along the direction of Z axis on the vertical plane and for measuring Y axis magnetic field toward the direction of Z axis on the YZ plane on a rectangular solid respectively can be developed, it can measure the magnetic gradient toward the direction of Z axis of X axis, Y axis and Z axis direction magnetic fields can be measured.

The fourth problem is to realize fine magnetic image mapping by developing array sensor elements consisting of a number of gradiometer elements with high density using a gradiometer element having a small cross section area of 5 mm×5 mm to 10 mm×10 mm compared to a SQUID element with that of 30 mm×30 mm.

The fifth problem is how to develop a small size gradiometer element comprising GSR elements, circuits and electrodes for a power source and input-output signals on the sensor board by means of an integrating circuit.

Means to Solve Technical Problems

The present inventor solved the first problem by the development of a newly designed gradiometer element for the magnetic field detection along the direction of Z axis described as below.

The GSR element includes two concave line-shape guides parallel to each other as a reference line, produced by photolithography method. The GSR element with two concave line-shape guides placed parallel to the magnetic wire on the GSR element board is called a parallel type GSR element. On the other hand, the GSR element with two concave line-shape guides placed vertical to the magnetic wire on the GSR element board is called a vertical type GSR element.

A board of a magnetic gradiometer element with more than three GSR elements includes two convex line-shape guides parallel to each other as a reference line, produced by photolithography method which are placed along the Z axis direction of gradiometer element.

More than three GSR elements with two concave line-shape guides are fitted on the gradiometer board along two convex line-shape guides towards Z axis direction to make its slide displacement of ±1 µm and angle mismatch of ±0.1 degree from the reference line. This high precise assembling can eliminate the outer magnetic noise to achieve the detectability of bio magnetism of 1 pT level without a magnetic shield room. Hereafter, this assemble is called a parallel type gradiometer element to detect the magnetic field gradient of the Z direction magnetic field toward the Z axis direction.

A SQUID can detect a minute magnetic field of 0.02 pT but the magnetic detection part is placed from the body surface by more than 30 mm because it is contained in its cryogenic temperature retainer. The gradiometer element can be placed within 5 mm from the body surface. It is seen that the living body magnetism decreases in inverse proportion to $1/(R+R_0)^2$. Therefore, the gradiometer with 1 pT level detectability can offer the same performance for detecting the living body magnetism as a SQUID with 0.02 pT level detectability.

The second problem is solved by setting micro rectangular parallelepiped stoppers produced by photolithography method stretching along the direction of X axis or Y axis on the gradiometer element with more than three micro coil elements arranged along the direction of Z axis. When the living body magnetism is measured by the gradiometer, the first axis direction, the second axis direction and third axis direction are treated as the same as Z axis direction, X axis direction and Y axis direction respectively. The stoppers are set at the designated distance from the body surface side end of the board with the accuracy of less than ±1 µm.

The source of living body magnetism is regarded as the current dipole. The magnetic gradient made by living body magnetic field is shown in the formula (1) dependent on the distance R from body surface.

$$H=(1/4\pi\mu_0) \times Ids \times 1/(R+R_0)^2 \qquad (1)$$

where H is the strength of magnetic field, R is the distance from living body surface in the direction of Z axis, Ro is the depth position of the source of magnetic field (current dipole), Ids is the current dipole, and $\mu_0$ is the permeability of vacuum. Formula (1) can be simplified to formula (2).

$$(1/H)^{1/2}=(4\pi\mu_0/Ids)^{1/2} \times (R+R_0) \qquad (2)$$

It means that $(1/H)^{1/2}$ is proportional to $(R+R_0)$.

The depth position of the source of living body magnetism can be computed by using the formula accompanied with the data on between the magnetic field measured values at the designated distance.

Figure 7:
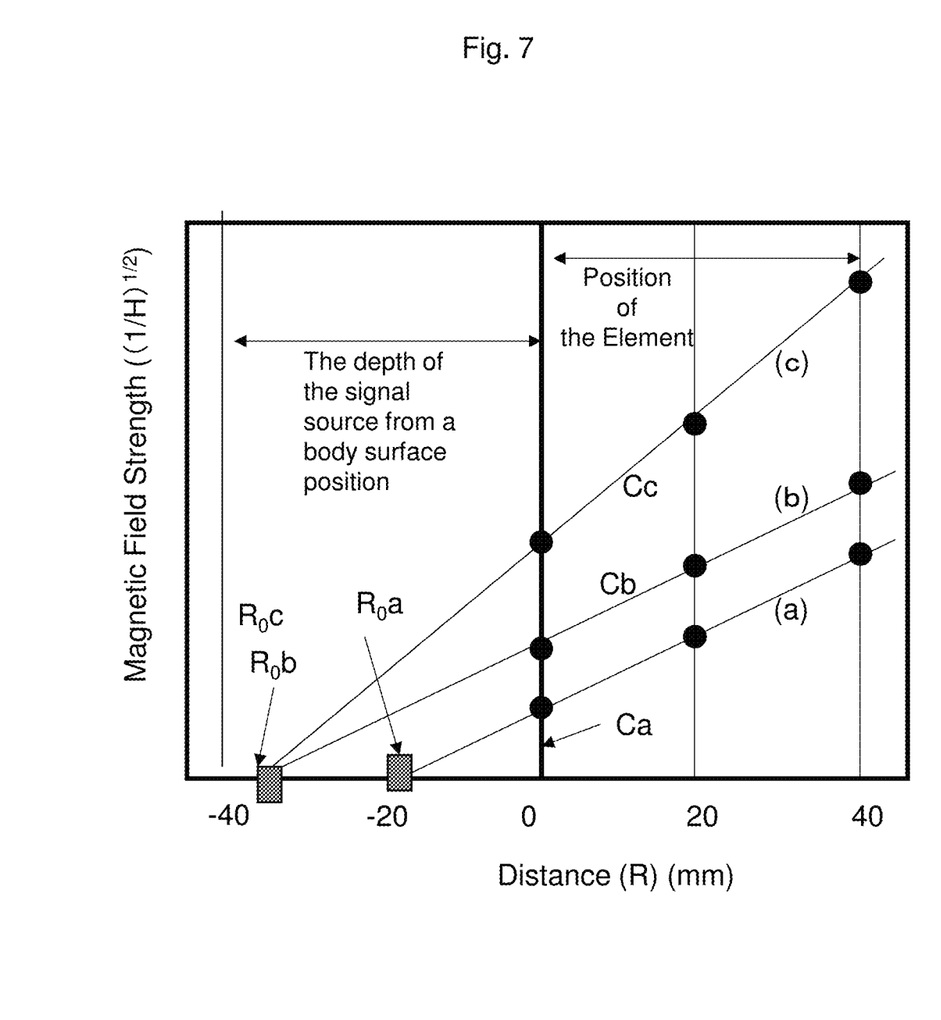
FIG. 7 is a diagram showing the calculation method for the depth position of a source of living body magnetism using the data obtained by the gradiometer.

This relationship between the magnetic field strength H and the distance R is shown in FIG. 7. The magnetic field strength of a living body surface can be determined by the magnetic field strength at the distance position of 0 mm. The depth position of current dipole of magic field source can be obtained from the intersection with a straight line and horizontal axis. The strength of current dipole can be calculated by the gradient of the straight line. That is, if the gradient is C, Ids is given by the formula of $Ids=4\pi\mu_0/C^2$.

The relationship shown by FIG. 7 can make clear the strength and the depth position of the current dipole.

Comparing the cases of (a), (b) and (c) which have the same measured values at a body surface position of 0 mm and different gradients or different depths, the cases of (a) and (b) have the same strength but different depth positions of the current dipole. The cases of (b) and (c) have the same depth position of dipole, but the strength of the current dipole.

The above discussion makes sure that gradiometer is effective to obtain the more detailed total image of body magnetism.

The third problem is solved by the development of a vertical type GSR element with a less than 3 mm length wire of X axis direction and two parallel convex line-shape guides along the Z axis direction.

Plural vertical type GSR elements are fitted on the gradiometer board with two concave line-shape guides on the vertical plane of the rectangular solid which has one or more vertical planes to the living body surface. This assembled plural vertical type GSR elements become a vertical type gradiometer element to detect the magnetic field gradient of the X direction magnetic field toward the Z axis direction. When this vertical type gradiometer element sets on the vertical plane of the rectangular solid, this assemble becomes a vertical type gradiometer element to detect the magnetic field gradient of X direction magnetic field against the Z axis direction.

A 3 dimensional gradiometer element comprises two vertical type GSR elements set on two vertical planes with vertical relationship as X axis and Y axis and one parallel type GSR element set on one vertical plane.

The micro-rectangular-parallelepiped-shape stoppers are arranged at the same positions with the center part of the parallel type GSR element and the wire positions of two vertical type GSR elements in order to keep the same measuring position from the body surface for three types GSR sensor elements.

The magnetic gradiometer sensor using GSR sensor is formed by assembling the gradiometer element with an electric circuit set in a space of the gradiometer element board. It achieves a 3 dimensional gradiometer with a length of less than 40 mm and the cross section of less than 5 mm by 5 mm which has a 36 times higher density than that of a SQUID.

It is also possible to form a gradiometer element to detect three axis magnetic field which has two vertical type and one parallel type gradiometer elements on one side called two or three vertical planes respectively.

The fourth problem is solved by the development of a micro coil with a pitch of 1 µm to 5 µm which can archive a high performance GSR element with the detectability of 1 pT level to the magnetic field and a magnetic wire length of less than 3 mm and a small sized gradiometer of less than 40 mm length and 5 mm to 10 mm width.

Figure 6:
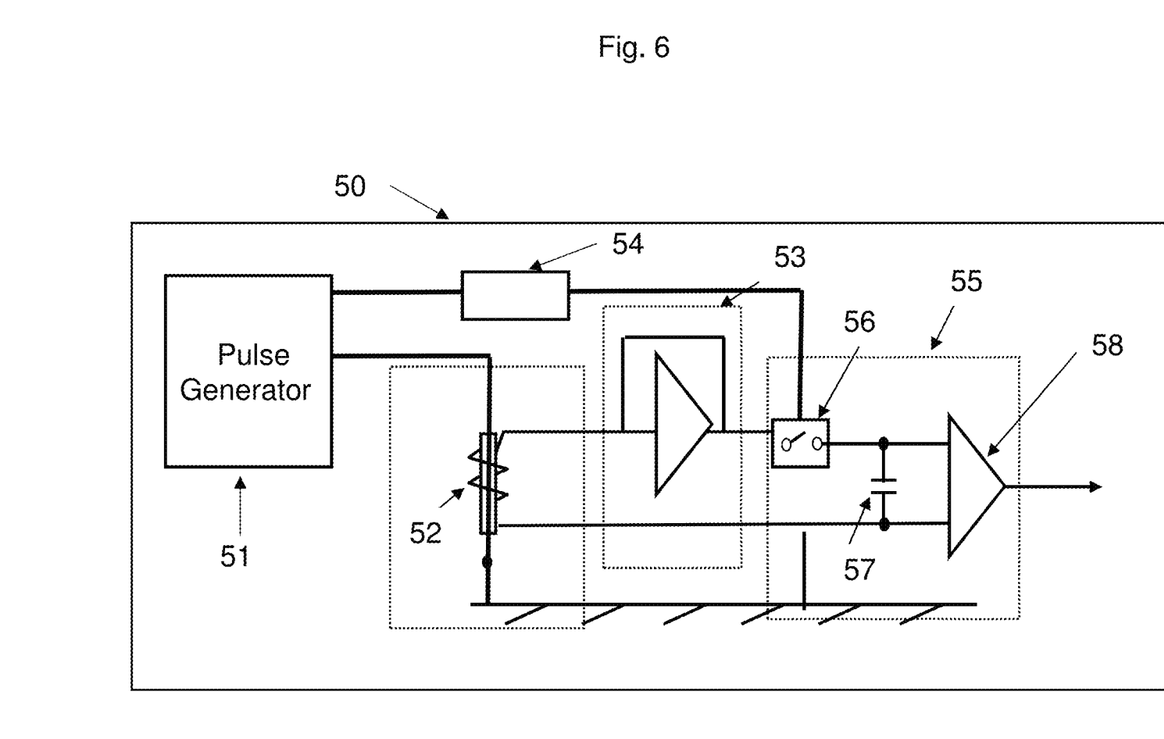
FIG. 6 shows a circuit block of the electronic circuit of the gradiometer.

The fifth problem is solved by the development of a close arrangement with a wiring length as short as possible between the micro coil and it is formed as an ASIC type electronic circuit by integrating the circuit shown in FIG. 6 which can suppress noise generation caused from GHz palace signals between the micro coil element and the electronic circuit.

Moreover, plural GSR elements used in the gradiometer have the same magnetic detectability. The electrodes for the power source and input-output signals are set on the gradiometer board at the opposite side to the body surface side.

By the way, the present invention uses GSR sensor as an ultra-high sensitive micro magnetic sensor but any ultra-high sensitive micro magnetic sensors with a micro coil element to detect magnetic field can be used in the invention.

Effect of the Invention

The gradiometer to detect three axis magnetic field of the present invention can achieve a handy-type diagnosis equipment used for magneto cardiogram and magnetoencephalography without a cryogenic temperature retainer or a magnetic shield room with the magnetic field detectability of 1 pT level from a living body. It can obtain the depth and direction of the source of living body magnetism computed by a three dimensional magnetic field data and offer fine magnetic image mapping measured by a higher density array sensor with a large number of pixels using small size GSR elements. It is expected that the performance of the present 3 axis type can achieve more accurate diagnosis of disease.

DESCRIPTION OF EMBODIMENTS

Embodiment 1

The object of this invention is three dimensional detection of living body magnetism. Embodiments of the present invention are described using the attached drawings where the magnetic field is divided to three components consisting of the first axis direction magnetic field (hereafter "Z axis magnetic field"), along the perpendicular direction on the body surface, the second axis direction magnetic field (hereafter "X axis magnetic field") along the horizontal direction perpendicular to Z axis direction and the third axis direction magnetic field (hereafter "Y axis magnetic field") perpendicular to the X and Z axis directions.

The first preferred embodiment of the present invention on the parallel type magnetic gradiometer element to detect the field strength and the gradient of Z axis magnetic field toward Z axis direction is described as below using FIG. 1.

The embodiment comprises a parallel type magnetic gradiometer board, plural parallel type GSR elements fitted on the board, an electronic circuit processing the output signal of GSR elements and electrodes connecting to outside circuit. The board includes two parallel micro convex line guides extending toward the direction of Z axis. The GSR element includes magnetic wires with electric conductivity, micro coils wound around the wire, two wire electrodes connected to the wires and two electrodes connected to the micro coils to the detect coil voltage and two concave line-shape guides parallel to the magnetic wire.

Each GSR element has the magnetic wire with an anisotropy field of less than 10 G and circumferential direction spin arrangement on the wire surface and is operated by current plus with the frequency of 0.5 GHz to 4.0 GHz. Its current intensity needed makes a circumferential direction magnetic field of more than 15 G which is 1.5 times larger than the wire surface anisotropy field of 10 G.

The board includes two parallel micro convex-line shape guides along the Z axis direction with high accuracy to make the slide displacement of less than ±1 μm and angle mismatch of less than 0.01 degree between the magnetic wires of plural GSR elements fitted on the convex-line shape guide.

In addition, the board includes the same number of micro rectangular parallelepiped stoppers as that of GSR elements produced by photolithography method stretched to the direction of X axis. The vertical type gradiometer element made by plural GSR elements on the board assembled with high accuracy can achieve the measurement of the magnetic gradient of the Z axis magnetic field strength toward the Z direction.

The two parallel micro concave line-shape guides extending in parallel to the magnetic wire on the GSR sensor element along Z axis direction have a concave width of less than 30 μm, a depth of less than 20 μm with the accuracy of less than 1 μm. Its desirable size is 5 μm to 10 μm in width, 5 μm to 15 μm in depth and the accuracy of less than 0.5 μm.

The two parallel micro convex line-shape guides extending 20 mm to 35 mm in parallel with magnetic wire on the GSR sensor element along the Z axis direction have a convex width of less than 30 μm, a height of less than 20 μm with the accuracy of less than 1 μm. Its desirable size is 4 μm to 9 μm in width, 4 μm to 14 μm in depth and less than 0.5 μm in accuracy. Its pedestal part has a width of less than 50 μm and a thickness of less than 20 μm.

The term "micro" as in a micro coil element, a micro convex line shape guide, and a micro concave line shape guide means a micro size with a remarkably excellent accuracy of less than 1 μm produced by photolithography method.

The two parallel micro convex line shape guides on the board of parallel type gradiometer element become the reference line along the direction of Z axis. When the plural parallel type GSR elements are fit on the convex line shape guides, the error between the reference line and the wire direction of GSR elements becomes less than ±1 μm in slide displacement and less than 0.01 degree of angle mismatch. The desirable level of the error is less than ±1 μm in slide displacement and less than 0.005 in angle mismatch. This enables detection of less than 1 pT level of body magnetism in the direction of Z axis without a magnetic shield room.

The size of the gradiometer is kept to be less than 50 mm in length including the part of the electrodes for external connection and from 5 mm to 10 mm in width using the shortest possible GSR element. It is desirable to be less than 30 mm in length. The magnetic field detectability has a trade off relationship with the length of magnetic wire. The shorter the length, the lower the magnetic field detectability. A GSR element with a coil pitch of 1 μm to 5 μm is desired to solve the tradeoff problem and to obtain the detectability of 1 pT level under conditions of small size GSR element with a magnetic wire length of less than 3 mm and a width of less than 3 mm.

The gradiometer board has the electronic circuit placed in the space between the plural parallel type GSR elements arranged along the direction of Z axis and the electrodes for connection to the external circuit attached to the opposite side of the board against the body surface. It is desirable that the electronic circuit is microminiaturized by an integrated-circuit and is placed close to the GSR elements for making the connection part length as short as possible.

The electronic circuit comprises a pulse generator, a micro coil element (GSR element), a buffer circuit with high frequency characteristics, a pulse timing regulator, a sample hold circuit, an electronic switch and an amplifier. The pulse generator generates pulse with frequency of 0.1 GHz to 5 GHz and supplies it to the wire wound by the micro coil which detects the voltage proportional to the external magnetic field strength and sends the signal voltage to the buffer circuit and then to the sample hold circuit. In the sample hold circuit, the peak voltage of the coil voltage wave is detected using the electronic switch controlled by the timing regulator and then amplified by the amplifier.

Micro rectangular parallelepiped shaped stoppers are equipped on the gradiometer board which are used for setting the plural GSR elements at the designated position along the direction of Z axis on the convex line-shape guides. The accuracy of the micro rectangular parallelepiped shaped stoppers is kept to be less than 1 μm.

The size of the stoppers is less than 200 μm in width and less than 100 μm in thickness. The desirable size is less than 50 μm in width, less than 34 μm in thickness and the same height of the micro convex line shape guides.

The arrangement of plural GSR elements using plural stoppers can achieve the designated distance from the body surface side with the accuracy of less than ±1 μm.

GSR element of the body surface side is placed at a distance of less than 5 mm from the living body surface. The desirable distance is less than 2 mm and as small as possible. GSR element can be set close to the living body surface by developing a thin gradiometer package using a thin protective film.

Though a SQUID can detect a minute magnetic field of 0.02 pT, the position of magnetic field detection part is separated from the body surface side by more than 30 mm. While the invention of the first embodiment achieves the detectability of 1 pT level, it can be set within 5 mm of the body surface so as to have the same detectability of living body magnetism as that of SQUID.

More than three GSR elements are arranged along the direction of Z axis and measure the magnetic field strength at the designated position from the body surface so that the depth position of the source of magnetic field can be computed using the formula (2) with those measured values. Considering the source of a cardiac magnetic field or brain magnetic field is from 10 mm to 40 mm in depth from the body surface, GSR element from the body surface side is placed at a distance of less than 5 mm from the living body. In addition, the desirable distance is about 2 mm and the desirable length of the gradiometer element is about 40 mm.

Therefore, the invention of the first embodiment makes it possible to obtain the total image of a living body magnetic field by calculating the depth position of the source of the magnetic field with the magnetic gradient in the direction of Z axis.

Embodiment 2

Figure 2:
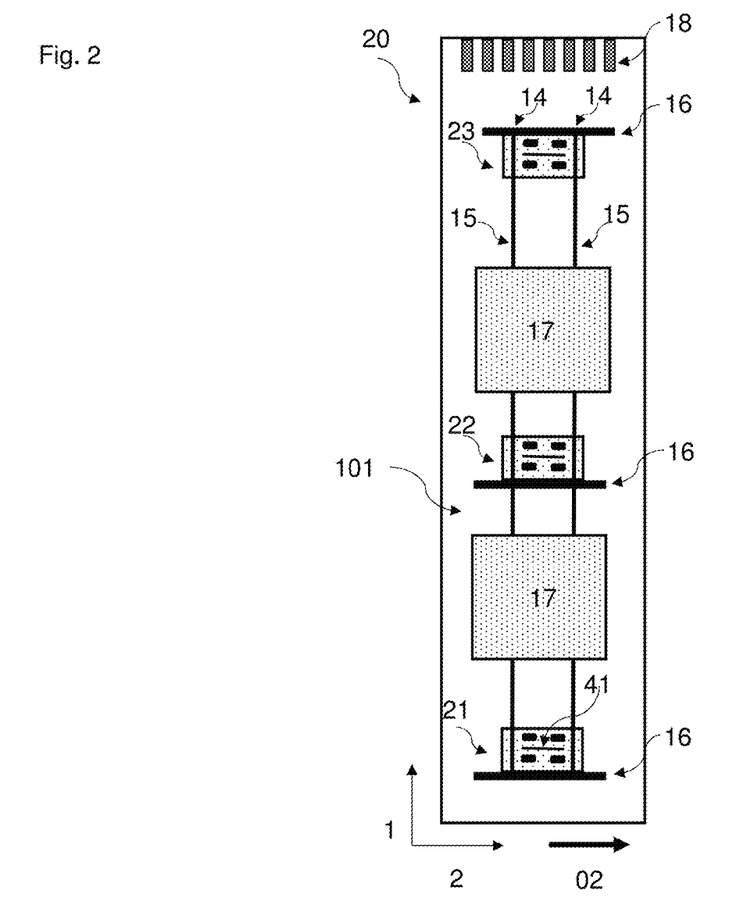
FIG. 2 is a schematic plane view of a vertical type gradiometer element related to Embodiment 2.

The second preferred embodiment of the present invention on the vertical type magnetic gradiometer element to detect the field strength and the gradient of X axis magnetic field toward Z axis direction is described as below using FIG. 2.

The embodiment comprises a vertical type magnetic gradiometer board, plural vertical type GSR elements fitted on the board, an electronic circuit processing the output signal of GSR elements and electrodes connecting to an outside circuit.

The board includes two parallel micro convex line guides extending along the Z axis direction, the GSR element having magnetic wires with electric conductivity, micro coils wound around the wire, two wire electrodes connected to the wires and two electrodes connected to the micro coils to detect coil voltage and two concave line-shape guides vertical to the magnetic wire.

The board includes two micro convex-line shape guides along the Z axis direction in parallel with high accuracy to make a slide displacement of less than ±1 μm and an angle mismatch of less than 0.01 degree among the magnetic wires of the plural GSR elements fitted on the convex-line shape guide.

Each GSR element has the magnetic wire with an anisotropy field of less than 10 G and circumferential direction spin arrangement on the wire surface and is operated by current plus with the frequency of 0.5 GHz to 4.0 GHz. Its current intensity needed makes a circumferential direction magnetic field of more than 15 G which is 1.5 times larger than the wire surface anisotropy field of 10 G.

In addition, the board has the same number of micro rectangular parallelepiped stoppers as that of vertical type GSR elements produced by photolithography method stretched along the X axis direction. The assembly of plural GSR elements set on the board with high accuracy in distance from living body surface can achieve the measurement of the magnetic gradient of the X axis magnetic field strength toward the Z direction.

The board with two parallel micro convex-line shape guides along the Z axis direction with high accuracy to make a slide displacement of less than ±1 μm and an angle mismatch of less than 0.01 degree among the magnetic wires of plural GSR elements fitted on the convex-line shape guide of which accuracy is the same level as that of Embodiment 1. This enables detection of less than 1 pT level of body magnetism in the direction of Z axis without a magnetic shield room.

Some design parameters such as the size of the gradiometer, the electric circuit, the electrode micro rectangular parallelepiped shaped stoppers and the position set for GSR elements are the same as that of the first embodiment.

Though a SQUID can detect a minute magnetic field of 0.02 pT, the size of magnetic field detection part is too large and it cannot detect the gradient of X axis magnetic field toward the Z axis direction. However, the invention of the second embodiment offers the small size and a close distance of less than 5 mm from the living body surface and achieves detectability of 1 pT level of the X axis magnetic field as well as the gradient toward the Z axis direction.

More than three GSR elements are arranged along the direction of Z axis and measure the magnetic field strength at the designated position from the body surface so that the depth position of the source of the magnetic field can be computed using the formula (2) with those measured values. Considering the source of a cardiac magnetic field or brain magnetic field is from 10 mm to 40 mm in depth from the body surface, the GSR element from the body surface side is placed at the distance of less than 5 mm from living body. In addition the desirable distance is about 2 mm and the desirable length of the gradiometer element is about 40 mm.

Therefore, the invention of the second embodiment makes it possible to obtain the total image of a living body magnetic field by calculating the depth position of the source of X axis magnetic field with the magnetic gradient toward the direction of Z axis.

Embodiment 3

Figure 3:
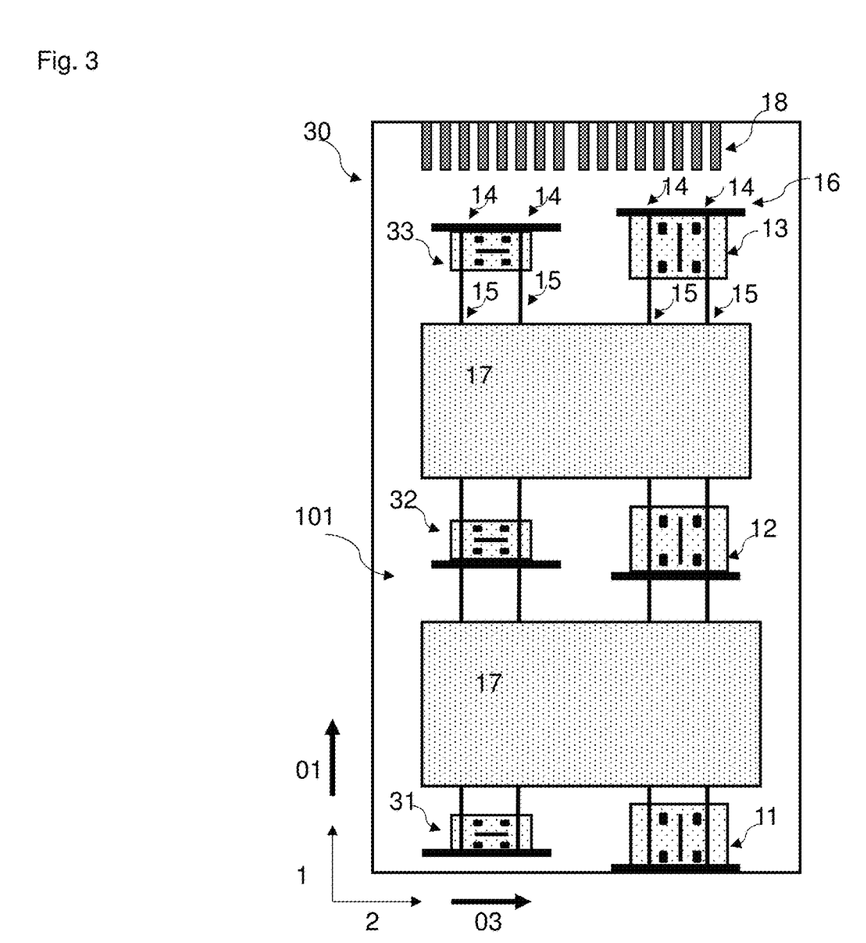
FIG. 3 is a schematic plane for 3 axis type gradiometer element in Embodiment 3.

The third preferred embodiment of the present invention on the 3 axis type magnetic gradiometer element to detect the field strength and the gradient of X, Y, Z axis magnetic fields toward the Z axis direction is described as below using FIG. 3.

This 3 axis type gradiometer element comprises:
(a) one parallel gradiometer element of the first embodiment placed on the first plane stretched along the first axis direction of the rectangular element body to detect the magnetic field gradient of the Z axis magnetic field toward the Z axis direction;
(b) one vertical type gradiometer element of the second embodiment placed on the second plane stretched along the Z axis direction of the rectangular element body to detect the magnetic field gradient of the X axis magnetic field toward the Z axis direction;
(c) one vertical type gradiometer element of the second embodiment placed on the third plane stretched along the Z axis direction of the rectangular element body to detect the magnetic field gradient of the Y axis magnetic field toward the Z axis direction.

The 3 axis type gradiometer element is formed by combining two vertical type gradiometer elements and parallel type gradiometer element on three vertical planes of the rectangular element body respectively. It can detect three axis magnetic field gradients toward the Z axis direction.

The 3 axis type gradiometer elements made from vertical and parallel types are placed at the same designated position from a living body surface using the stoppers. The electronic circuits are set in the space on the board except the elements and the guides. The board size is under 40 mm in length and under 5 mm×5 mm in cross section. It can achieve high density magnetic image, about 36 times higher than that of a SQUID type.

Though a SQUID can detect a minute magnetic field of 0.02 pT, the position of the magnetic field detection part is separated from the body surface side by more than 30 mm. While the invention of the second embodiment achieves the detectability of 1 pT level, it can be set within 5 mm from the body surface so as to have the same detectability of living body magnetism.

Embodiment 3

The third preferred embodiment of the present invention on the 3 axis type magnetic gradiometer element can have another design that comprises:
(a) one parallel gradiometer element and one vertical type gradiometer element placed on the first plane stretched along the Z axis direction of the rectangular element body to detect the magnetic field gradient of the Z and X axis magnetic field toward the Z axis direction respectively;
(b) one vertical type gradiometer element placed on the second plane stretched along the Z axis direction of the rectangular element body to detect the magnetic field gradient of the Y axis magnetic field toward the Z axis direction.

Therefore, the invention of the third embodiment makes it possible to obtain the direction and the depth position of the current dipole as the source of the magnetic field and the total image of living body magnetic field by calculating the magnetic gradient of X axis, Y axis and Z axis magnetic fields toward the Z axis direction.

Embodiment 4

The fourth preferred embodiment of the present invention on the 3 axis type magnetic gradiometer comprises:

(a) any gradiometer element of the parallel type, the vertical type and 3 axis type;
(b) an electric circuit for processing the output signal of GSR elements; and
(c) a CPU existing outside the board which is connected to the circuit through electrodes set on the board.

The gradiometer system including the CPU and an installed program calculates the direction and the depth of the current dipole as the magnetic source of the living body. When an array type of magnetic gradiometers are used, it can calculate the magnetic image mapping or current dipole mapping used for magnetoencephalography and magneto cardiogram.

EXAMPLES

Example 1

Figure 1:
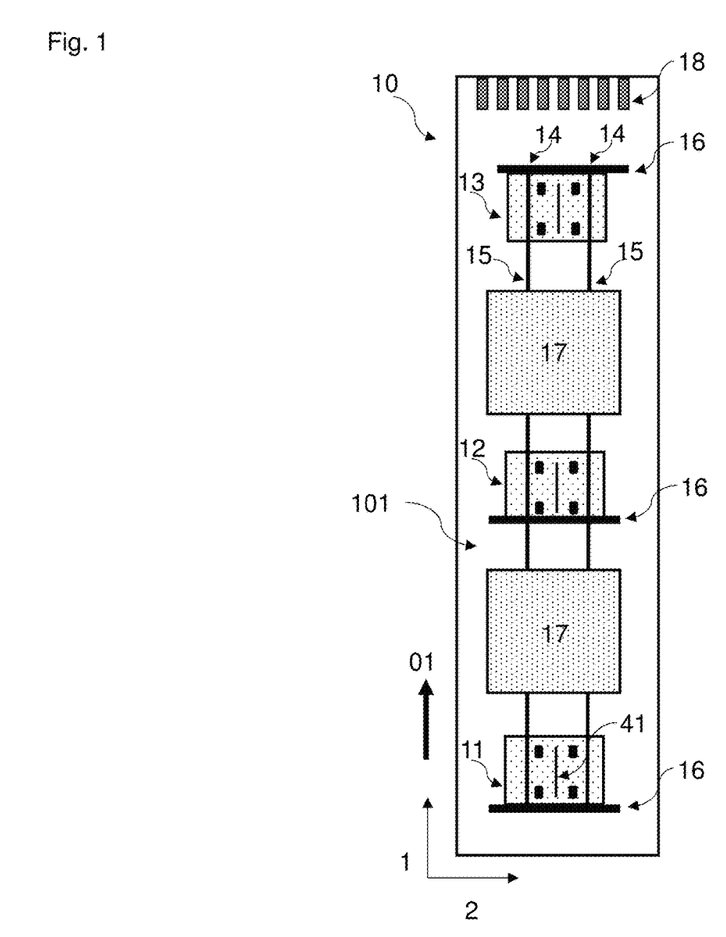
FIG. 1 is a schematic plane view of a parallel type gradiometer element related to Embodiment 1.

Example 1 of the present invention on the parallel type magnetic gradiometer element is described in detail using FIGS. 1, 4, 5a, 5b, 6 and 7. FIG. 1 is a schematic plane view of a parallel type gradiometer element. The gradiometer element 10 of Embodiment 1 comprises a parallel type magnetic gradiometer board 101, plural parallel type GSR elements fitted on the board, an electronic circuit for processing the output signal of GSR elements and the electrodes 18 connecting to an outside circuit.

FIG. 1 shows that the board 101 is equipped with two parallel micro convex line guides 15 extending toward the direction of Z axis 1 and three GSR elements 11, 12, 13 are fitted on the convex line guides 15 at the place of the lower 11, the middle 12 and upper sides 13 from the living body surface. The space among the elements is used for setting the electronic circuit 17. The micro-rectangular-parallelepiped-shape stoppers 16 are disposed along the X axis direction and electrodes 18 are set on the upper side end of the board 101.

Figure 4:
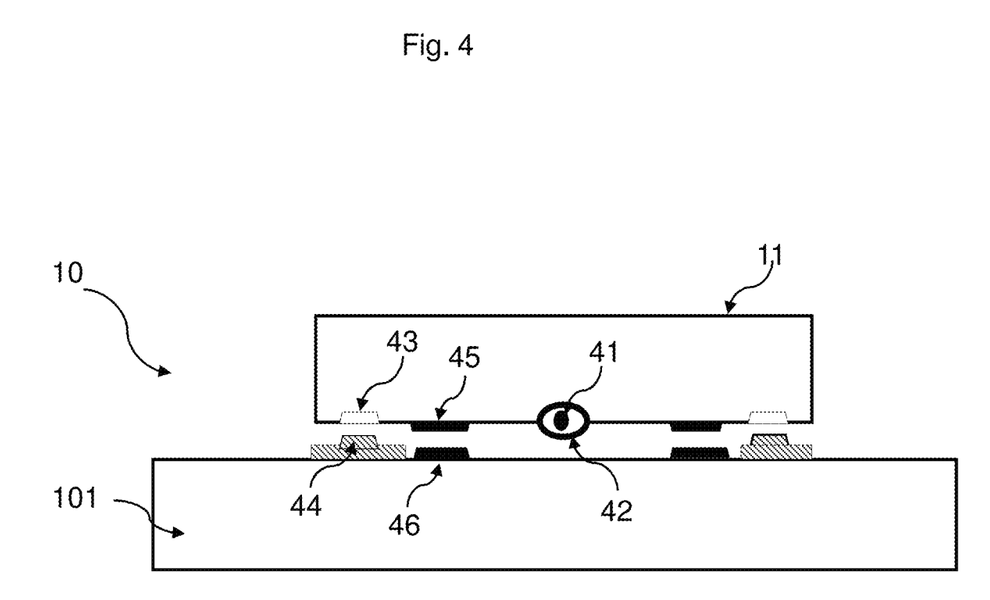
FIG. 4 is a schematic cross-section view of a parallel type gradiometer element related to Embodiment 1.
Figure 5:
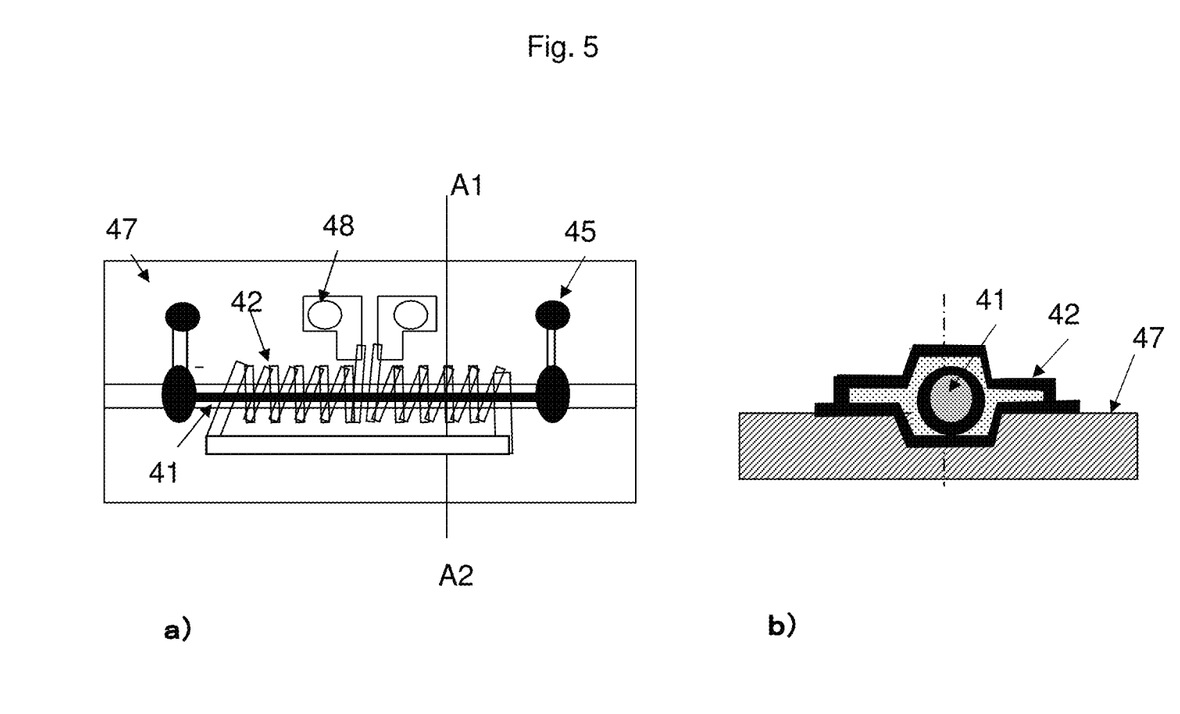
FIGS. 5a and 5b are schematic structure views of a GSR element with a micro coil element.

The GSR element is equipped with a magnetic wire 41 with electric conductivity, micro coils 42 wound around the wire, two wire electrodes 45 connected to wires and two electrodes 48 connected to micro coils to detect the coil voltage and two concave line-shape guides 14 vertical to magnetic wire which is shown as concave line-shape guides 43 in FIG. 4 and FIG. 5.

When the three parallel type GSR elements 11, 12, 13 fit to the convex line shape guides 44 on the board 101 stretched along the wire direction 01 using the two concave line-shape guides 43, the wire direction matches the Z axis direction and three elements have the same sensitivity to the Z axis direction magnetic field. This result can achieve perfect cancellation of the external magnetic field noise.

The difference between the reference line and the wire direction of GSR element becomes less than ±1 µm in slide displacement and less than 0.01 degree in angle mismatch. The desirable level of the error is less than ±1 µm in slide displacement and less than 0.005 in angle mismatch. This enables detection of less than 1 pT level of living body magnetism in the Z axis direction without using a magnetic shield room.

The GSR element has a length of 2.5 mm, a width of 2 mm and a thickness of 0.2 mm which comprises the board 47, the glass coating amorphous wire 41 with the diameter of 10 µm, the length of 2 mm and glass thickness of 1 µm, the coil with the coil pitch of 2 µm.

The examples of the present invention use GSR elements equipped with an amorphous wire with an anisotropy of 8 G as the micro coil element of ultra-sensitive micro magnetic sensor and operate it by the pulse current with a frequency of 1.5 GHz and an intensity of 200 mA.

By the way the GSR element is characterized by having a magnetic wire with an anisotropy field of less than 10 G and circumferential direction spin arrangement on the wire surface and to be operated by plus current with a frequency of 0.5 GHz to 4.0 GHz and a pulse current intensity enough to make the circumferential direction magnetic field 1.5 times larger than the anisotropy field of the wire surface.

Two parallel micro convex line-shape guides 15 with the width of 9 µm and the height of 7 µm with the accuracy of 0.5 µm in parallel to magnetic wire on the gradiometer board 101 along Z axis direction are produced by photolithography method. Two parallel micro concave line-shape guides 14 have the width of 10 µm and the depth of 7 µm with the accuracy of 0.5 µm.

Two parallel micro convex line shape guides 15 on the board of parallel type gradiometer element are regarded as the reference line along the direction of Z axis. When plural parallel type GSR elements fit on the convex line shape guides 15, the difference between the reference line and the wire direction of GSR element becomes ±0.4 µm in slide displacement and less than 0.0104 degree of angle mismatch. This enables detection of less than 1 pT level of living body magnetism along the Z axis direction without a magnetic shield room.

The size of the gradiometer is 40 mm in length including the electrodes 18 for external connection and 5 mm in width using the smallest possible GSR elements. The magnetic field detectability has a tradeoff relation with the length of the magnetic wire. The shorter the length, the lower the magnetic field detectability. When the GSR element has a coil pitch of 2 µm, a small sized GSR element with a magnetic wire length of 2 mm and a width of 0.6 mm can achieve the detectability of 1 pT level.

The gradiometer board has the electronic circuits 17 placed in the space between the plural parallel type GSR elements arranged along the Z axis direction and the electrode 18 connected to the external circuit on the opposite side of the board against the living body surface. Each electronic circuit 17 is miniaturized by an integrated-circuit with the size of 1 mm×1 mm to be placed at the distance of 100 µm from the GSR elements for making the connection wire as short as possible.

The electronic circuit 50 comprises a pulse generator 51, a GSR element 52, a buffer circuit 53 with a high frequency band, a pulse timing regulator 54, a sample hold circuit 55, an electronic switch 56 and an amplifier 58. The pulse generator generates a pulse frequency of 1.5 GHz and supply it to the wire 41 wound by a micro coil which detects the voltage proportional to the external magnetic field strength and sends to the buffer circuit 53 and then to the sample hold circuit 55. In the sample hold circuit, the peak voltage of the coil voltage wave is detected using the electronic switch 56 controlled by the timing regulator 54 and then amplified by the amplifier 58. Here the coil has a large resistance of 2 KΩ to reduce the current intensity passing through the coil. So the coil voltage is reduced minimally or only by 5%.

Micro rectangular parallelepiped shaped stoppers 16 are disposed on the gradiometer board 101 to set the plural GSR elements at the designated position of 2 mm, 16 mm and 36 mm from the living body surface, respectively, along the Z axis direction on the convex line-shape guides.

The dimensional accuracy of the micro rectangular parallelepiped shaped stoppers is kept to be 0.5 µm. The dimensions of the stoppers are 50 µm in width and 14 µm in thickness. The thickness is the same as the height of micro convex line shape guides. The arrangement of the plural GSR elements using plural stoppers can set the designated distance from the body surface side with an accuracy of less than ±0.5 μm.

The GSR element 11 is placed at the distance of 2 mm from the body surface. The close distance from the body surface can be achieved by developing the thin gradiometer package using a thin protective film.

Though a SQUID can detect a minute magnetic field of 0.02 pT, the position of the magnetic field detection part is separated from the body surface by more than 30 mm. Example 1 achieves the detectability of 1 pT level. While the invention of the first embodiment achieves the detectability of 1 pT level, it can be set within 5 mm of body surface so as to have the same detectability of living body magnetism as that of SQUID.

Three GSR elements are arranged along the Z axis direction and measure the magnetic field strength at the designated position from the body surface so that the depth position of the source of magnetic field can be computed using the formula (2) and those measured values. Considering the source of a cardiac magnetic field or brain magnetic field is from 10 mm to 40 mm in depth from the body surface, the length of the gradiometer element is set to 40 mm and GSR element by lower side is placed at the distance of 2 mm from the living body surface.

Example 2

Example 2 of the present invention on the vertical type magnetic gradiometer element is described as below using FIG. 2.

It can detect the field strength and the gradient of the X axis magnetic field toward the Z axis direction by arranging three GSR elements on the board to keep the wire direction 02 along the second direction (X axis direction) at the position of the lower, the middle and upper side from the living body surface.

The board includes two parallel micro convex line guide 15 extending toward the Z axis direction. The GSR element includes two concave line-shape guides 14 vertical to magnetic wire. Both parts are fitted using the convex line guide 15 and the concave line-shape guides 14. The assembly can arrange the wire direction 02 same as the second direction (X axis direction) to make the same sensitivity among the three elements and cancel the outer magnetic field noise.

The accuracy of the assembly is achieved to be the same level as that of Example 1. This enables detection of the X axis magnetic field strength of less than 1 pT level of living body magnetism toward the Z axis direction without a magnetic shield room.

Some design parameters such as the size of the gradiometer, the electric circuit, the electrode micro rectangular parallelepiped shaped stoppers and the position set for the micro coil elements are the same as that of Example 1.

Though a SQUID can detect a minute magnetic field of 0.02 pT, the size of magnetic field detection part is too large and it cannot detect the gradient of the X axis magnetic field toward the Z axis direction.

However, the invention of Example 2 offers the small size and the close distance of less than 5 mm from the living body surface and achieves the detectability of 1 pT level of the X axis magnetic field.

Three GSR elements are arranged along the direction of Z axis and measure the magnetic field strength at the designated position from the living body surface so that the depth position of the source of magnetic field can be computed using the formula (2) and those measured values.

Therefore, Example 2 makes it possible to obtain the total image of a living body magnetic field by calculating the depth position of the source of the X axis magnetic field with the magnetic gradient toward the Z axis direction.

Example 3

Example 3 is a 3 axis type magnetic gradiometer element to detect the field strength and the gradient of X, Y, Z axis magnetic field toward to Z axis direction. It is designed to combine one parallel type gradiometer element in FIG. 1 and two vertical type gradiometer elements shown in FIG. 2.

There are two kinds of the 3 axis type gradiometer element. The first one is to set one parallel type gradiometer element in FIG. 1 and two vertical type gradiometer elements shown in FIG. 2 on the three vertical planes of the rectangular element body along the Z axis direction respectively. The second is to set one parallel/vertical combined type gradiometer element shown in FIG. 3 and one vertical type gradiometer element on the two vertical planes of the rectangular element body along the first axis direction respectively.

The first one comprises:
(a) one parallel gradiometer element placed on the first plane stretched along the Z axis direction of the rectangular element body to detect the magnetic field gradient of the Z axis magnetic field toward the Z axis direction;
(b) one vertical type gradiometer element placed on the second plane stretched along the Z axis direction of the rectangular element body to detect the magnetic field gradient of the X axis magnetic field toward the Z axis direction; and
(c) one horizontal type gradiometer element placed on the third plane stretched along the Z axis direction of the rectangular element body to detect the magnetic field gradient of the Y axis magnetic field toward the Z axis direction.

The second one comprises:
(c) one parallel gradiometer element and one vertical type gradiometer element placed on the first plane stretched toward the Z axis direction of the rectangular element body to detect the magnetic field gradient of the Z and X axis magnetic field toward the Z axis direction respectively;
(d) one vertical type gradiometer element placed on the second plane stretched along the Z axis direction of the rectangular element body to detect the magnetic field gradient of the Y axis magnetic field toward the Z axis direction.

Example 3 has common electric circuits 17. The electrodes 18 are set on the top plane of the rectangular element body. All GSR elements are fitted to keep the wire direction the same. They are set at the designated positions such as the lower 21, 31, the middle 22, 32 and the upper sides 13, 33 using the micro rectangular parallelepiped shaped stoppers 16 set at the distance of 2 mm, 16 mm and 36 mm from the bottom plane (surface of the living body).

The electronic circuits 17 are placed in the empty space of the boards free from GSR elements. The 3 axis type magnetic gradiometer elements have the size with the length of 40 mm and with the cross section of 5 mm×5 mm to achieve 36 times higher density of the magnetic image than that of SQUID.

Though a SQUID can detect a minute magnetic field of 0.02 pT, the position of magnetic field detection part is separated from the body surface by more than 30 mm. While Example 3 achieves the detectability of 1 pT level, it can be set at the position of 2 mm from the living body surface so as to have the same detectability of three axis magnetic field of living body magnetism as that of SQUID.

Therefore, the invention of Example 3 makes it possible to obtain the direction and the depth position of current dipole as the source of magnetic field and the total image of the living body magnetic field by calculating the magnetic gradient of the X axis, Y axis and Z axis magnetic fields toward the Z axis direction.

Example 4

Example 4 of the present invention on the 3 axis type magnetic gradiometer comprises:
(a) any of the parallel type, the vertical type and 3 axis type gradiometer elements;
(b) the electric circuit processing the output signal of GSR elements; and
(c) a CPU existing outside the board which is connected to the circuit through the electrodes set on the board.

A gradiometer system including the CPU and an installed program calculates the direction and the depth of the current dipole as the magnetic source of the living body. When array type of magnetic gradiometers are used, they can calculate the magnetic image mapping or current dipole mapping used for magneto cardiogram and magnetoencephalography.

INDUSTRIAL APPLICABILITY

The gradiometer to detect three axis magnetic field of this invention has the magnetic field detectability of 1 pT level from a living body. It can achieve handy-type diagnosis equipment for magneto cardiogram and magnetoencephalography without a cryogenic temperature retainer or a magnetic shield room. More accurate diagnosis of disease can be expected using the depth and direction of the source of the living body magnetism which can be computed by three dimensional magnetic field data. The small size elements can make the arrangement with a higher density array to increase pixel counts of magnetic image mapping.

In future, the handy-type diagnosis equipment for magneto cardiogram and magnetoencephalography developed by the 3 axis type gradiometer of the preset invention will come into popular diagnosis equipment instead of Electrocardiogram and Electroencephalogram.

What is claimed is:

1. A parallel type gradiometer element to detect a magnetic field gradient of a first axis magnetic field toward a first axis direction, comprising:
a board with two convex line-shape guides stretched along the first axis;
a plurality of micro coil elements including magnetic wires, the plurality of micro coils wound around the magnetic wires, two coil terminals for detecting coil voltage, two wire terminals for conducting current through wires and two concave line-shape guides in parallel each other;
an electric circuit processing an output signal of GSR elements; and
a plurality of electrodes connecting to an outside circuit;
wherein the micro coil elements are fitted on the board using both of the convex line-shape guides of the boards and the concave line-shape guides of the elements to keep parallel lines between the wires of the micro coil elements with a side error of less than ±1 μm and an angle error of less than ±0.01 degree against the first axis direction.

2. The parallel type gradiometer element of claim 1, wherein the plurality of micro coil elements provide the wire with a circular spin aliment domain on the surface and an anisotropy field of less than 10 G and is operated by a pulse current frequency of 0.5 GHz to 4.0 GHz and a current strength needed to generate a circular magnetic field 1.5 times larger than the anisotropy field on the wire surface.

3. The parallel type gradiometer element of claim 1, wherein the board includes a plurality of rectangular parallelepiped shaped stoppers stretched along a second direction to keep distances of the micro coil elements from the living body side end to an accuracy of less than ±1 μm.

4. A gradiometer, comprising;
a plurality of gradiometer elements according to claim 1;
an electric circuit for processing an output signal of a plurality of GSR elements; and
a CPU existing outside of a board.

5. A vertical type gradiometer element to detect a magnetic field gradient of a second axis magnetic field toward a first axis direction, comprising
a board with two convex line-shape guides stretched along the first axis;
plural micro coil elements including magnetic wires, micro coils wound around the wires, two terminals for detecting coil voltage, two terminals for conducting current through wires and two concave line-shape guides stretched vertically in the wire direction in parallel with each other;
an electric circuit processing an output signal of GSR elements; and
electrodes connecting to an outside circuit;
wherein the micro coil elements are fitted on the board using both of the convex line-shape guides of the boards and the concave line-shape guides of the elements to keep parallel lines between the wires of the plural micro coil elements with a side error of less than ±1 μm and an angle error of less than ±0.01 degree against the first axis direction.

6. The vertical type gradiometer element of claim 5, wherein the micro coil element provides the wire with a circular spin aliment domain on the surface and anisotropy field of less than 10 G and is operated by a pulse current frequency of 0.5 GHz to 4.0 GHz and a current strength needed to generate a circular magnetic field 1.5 times larger than the anisotropy field on the wire surface.

7. The vertical type gradiometer element of claim 5, wherein the boards includes plural rectangular parallelepiped shaped stoppers stretched along the second direction to keep distances of the micro coil elements from the living body side end to the accuracy of less than ±1 μm.

8. A three axis type gradiometer element to detect three axis magnetic field gradients of the first axis, the second and the third axis magnetic fields toward the first axis direction comprising:
one parallel gradiometer element placed on the first plane stretched along the first axis direction of the rectangular element body to detect the magnetic field gradient of the first axis magnetic field toward the first axis direction, wherein the parallel gradiometer element includes a board with two convex line-shape guides stretched along the first axis; a plurality of micro coil elements including magnetic wires, the plurality of micro coils wound around the magnetic wires, two coil terminals for detecting coil voltage, two wire terminals for conducting current through wires and two concave line-shape guides in parallel each other; an electric circuit processing an output signal of GSR elements; and a plurality of electrodes connecting to an outside circuit; wherein the micro coil elements are fitted on the board using both of the convex line-shape guides of the boards and the concave line-shape guides of the elements to keep parallel lines between the wires of the micro coil elements with a side error of less than ±1 μm and an angle error of less than ±0.01 degree against the first axis direction;

a first vertical type gradiometer element placed on the second plane stretched along the first axis direction of the rectangular element body to detect the magnetic field gradient of the second axis magnetic field toward the first axis direction, wherein the vertical type gradiometer element includes a board with two convex line-shape guides stretched along the first axis; plural micro coil elements including magnetic wires, micro coils wound around the wires, two terminals for detecting coil voltage, two terminals for conducting current through wires and two concave line-shape guides stretched vertically in the wire direction in parallel with each other; an electric circuit processing an output signal of GSR elements; and electrodes connecting to an outside circuit; wherein the micro coil elements are fitted on the board using both of the convex line-shape guides of the boards and the concave line-shape guides of the elements to keep parallel lines between the wires of the plural micro coil elements with a side error of less than ±1 μm and an angle error of less than ±0.01 degree against the first axis direction; and a second vertical type gradiometer element placed on the third plane stretched along the first axis direction of the rectangular element body to detect the magnetic field gradient of the third axis magnetic field toward the first axis direction.

9. A three axis type gradiometer element to detect three axis magnetic field gradients of the first axis, the second axis and the third axis magnetic fields toward the first axis direction comprising:

one parallel gradiometer element and a first vertical type gradiometer element placed on the first plane stretched along the first axis direction of the rectangular element body to detect the magnetic field gradient of the first and second axis magnetic field toward the first axis direction respectively;

wherein the parallel gradiometer element includes a board with two convex line-shape guides stretched along the first axis; a plurality of micro coil elements including magnetic wires, the plurality of micro coils wound around the magnetic wires, two coil terminals for detecting coil voltage, two wire terminals for conducting current through wires and two concave line-shape guides in parallel each other; an electric circuit processing an output signal of GSR elements; and a plurality of electrodes connecting to an outside circuit; wherein the micro coil elements are fitted on the board using both of the convex line-shape guides of the boards and the concave line-shape guides of the elements to keep parallel lines between the wires of the micro coil elements with a side error of less than ±1 μm and an angle error of less than ±0.01 degree against the first axis direction;

a second vertical type gradiometer element placed on the second plane stretched along the first axis direction of the rectangular element body to detect the magnetic field gradient of the third axis magnetic field toward the first axis direction;

wherein each of the first and second vertical type gradiometer elements include a board with two convex line-shape guides stretched along the first axis; plural micro coil elements including magnetic wires, micro coils wound around the wires, two terminals for detecting coil voltage, two terminals for conducting current through wires and two concave line-shape guides stretched vertically in the wire direction in parallel with each other; an electric circuit processing an output signal of GSR elements; and electrodes connecting to an outside circuit; wherein the micro coil elements are fitted on the board using both of the convex line-shape guides of the boards and the concave line-shape guides of the elements to keep parallel lines between the wires of the plural micro coil elements with a side error of less than ±1 μm and an angle error of less than ±0.01 degree against the first axis direction.

* * * * *